United States Patent
Czaplewski et al.

(10) Patent No.: US 10,280,287 B2
(45) Date of Patent: *May 7, 2019

(54) FLAME-RETARDANT ACONITIC ACID-DERIVED SMALL MOLECULES

(71) Applicant: International Business Machines Corporation, Armonk, NY (US)

(72) Inventors: Sarah K. Czaplewski, Rochester, MN (US); Brandon M. Kobilka, Tucson, AZ (US); Joseph Kuczynski, North Port, FL (US); Jason T. Wertz, Pleasant Valley, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 30 days.

This patent is subject to a terminal disclaimer.

(21) Appl. No.: 15/611,237

(22) Filed: Jun. 1, 2017

(65) Prior Publication Data
US 2018/0346688 A1   Dec. 6, 2018

(51) Int. Cl.
*C08K 5/521* (2006.01)
*C08K 5/524* (2006.01)
(Continued)

(52) U.S. Cl.
CPC ............ *C08K 5/5393* (2013.01); *C08K 5/521* (2013.01); *C08K 5/5333* (2013.01);
(Continued)

(58) Field of Classification Search
None
See application file for complete search history.

(56) References Cited

U.S. PATENT DOCUMENTS 2,754,319 A * 7/1956 Johnston .............. C07F 9/4006
106/18.14
2016/0251485 A1   9/2016 Boday et al.

FOREIGN PATENT DOCUMENTS

| CN | 103965245 A | 8/2014 | |
| CN | 104356361 A | 2/2015 | |
| GB | 1482784 A * | 8/1977 | ......... H05K 3/0094 |

OTHER PUBLICATIONS

Mengal et al., "Citric acid based durable and sustainable flame retardant treatment for lyocell fabric," Carbohydrate Polymers, vol. 153, 2016, pp. 78-88, Elsevier. DOI: 10.1016/j.carbpol.2016.07.074.

(Continued)

*Primary Examiner* — Richard A Huhn
(74) *Attorney, Agent, or Firm* — Kelsey M. Skodje

(57) ABSTRACT

A flame-retardant aconitic acid-derived small molecule, a process for forming a flame-retardant polymer, and an article of manufacture comprising a material that contains a flame-retardant aconitic acid-derived small molecule are disclosed. The flame-retardant aconitic acid-derived small molecule can be synthesized from aconitic acid obtained from a bio-based source, and can have at least one phosphoryl or phosphonyl moiety with phenyl, allyl, or thioether substituents. The process for forming the flame-retardant polymer can include reacting an aconitic acid derivative with a flame-retardant phosphorus-based molecule to form a flame-retardant aconitic acid-derived small molecule, and combining the flame-retardant aconitic acid-derived small molecule with a polymer. The material in the article of manufacture can be a resin, adhesive, polymer, etc.

17 Claims, 15 Drawing Sheets

(51) Int. Cl.

| | | |
|---|---|---|
| *C07F 9/02* | (2006.01) | |
| *C08K 5/5393* | (2006.01) | |
| *C08K 5/5333* | (2006.01) | |
| *C08K 5/5399* | (2006.01) | |
| *C09J 9/00* | (2006.01) | |
| *C09J 11/06* | (2006.01) | |
| *H05K 1/03* | (2006.01) | |
| *C07C 69/007* | (2006.01) | |
| *C07F 9/113* | (2006.01) | |
| *C07F 9/09* | (2006.01) | |
| *C07C 69/003* | (2006.01) | |
| *C08K 5/00* | (2006.01) | |
| *C07F 9/141* | (2006.01) | |

(52) U.S. Cl.
CPC .............. *C08K 5/5399* (2013.01); *C09J 9/00* (2013.01); *C09J 11/06* (2013.01); *H05K 1/0353* (2013.01); *C07C 69/003* (2013.01); *C07C 69/007* (2013.01); *C07F 9/091* (2013.01); *C07F 9/093* (2013.01); *C07F 9/113* (2013.01); *C07F 9/1411* (2013.01); *C07F 9/1412* (2013.01); *C08K 5/0066* (2013.01); *C08K 5/524* (2013.01); *C08L 2201/02* (2013.01); *C08L 2666/84* (2013.01); *C09J 2203/326* (2013.01); *C09J 2205/102* (2013.01); *H05K 2201/012* (2013.01); *H05K 2201/0154* (2013.01)

(56) References Cited

OTHER PUBLICATIONS

Czaplewski et al., "Functionalized Flame-Retardant Aconitic Acid-Derived Molecules," U.S. Appl. No. 15/611,313, filed Jun. 1, 2017.
Czaplewski et al., "Flame-Retardant Aconitic Acid-Derived Cross-Linkers," U.S. Appl. No. 15/611,360, filed Jun. 1, 2017.
Czaplewski et al., "Flame-Retardant Aconitic Acid-Derived Monomers" U.S. Appl. No. 15/611,423, filed Jun. 1, 2017.
List of IBM Patents or Patent Applications Treated as Related, Signed Jun. 1, 2017, 2 pages.
"Poly Star UM 55", Poly vinyl chloride / Vinyl Acetate copolymer, Data Sheet, retrieved from kianresin.com, Sep. 2018, 2 pages.
Meyer et al., "The synthesis of citric acid phosphate," Journal of the American Chemical Society, 1959, 81, pp. 2094-2096 (Abstract Only).

* cited by examiner

C: Thiol-ene with 360, UV
D: Thiol-ene with 375, MeOH, UV
E: Thiol-ene with 345, MeOH, pH 9, UV

FLAME-RETARDANT ACONITIC ACID-DERIVED SMALL MOLECULES

BACKGROUND

The present disclosure relates to bio-renewable flame-retardant compounds and, more specifically, flame-retardant aconitic acid-derived small molecules.

Bio-based, sustainable compounds can be used in the syntheses of substances that previously required petroleum-based raw materials. Examples of uses for bio-based compounds include polymers, flame retardants, cross-linkers, etc. There are numerous strategies for efficiently and inexpensively producing bio-based compounds on an industrial scale. Examples of these strategies can be found in fermentation technologies, membrane technologies, and genetic engineering. Aconitic acid (propene-1,2,3-tricarboxylic acid) is one example of a bio-based compound that can have applications as a component of various polymers, resins, and small molecules. Aconitic acid is an intermediate in the citric acid cycle, wherein it is acted upon by the aconitase enzyme. Bio-based materials, such as sugarcane or citric acid, are common sources of aconitic acid.

SUMMARY

Various embodiments are directed to flame-retardant aconitic acid-derived small molecules. The flame-retardant aconitic acid-derived small molecules can have at least one phosphoryl or phosphonyl moiety and at least one substituent bound to the phosphoryl or phosphonyl moiety, wherein the substituent is selected from a group consisting of a phenyl substituent, an ally substituent, and a thioether substituent. The flame-retardant aconitic acid-derived small molecules can be synthesized from aconitic acid obtained from a bio-based source. Additional embodiments are directed to forming a flame-retardant polymer. The polymer can be produced by forming a phosphorus-based flame-retardant molecule, forming an aconitic acid derivative, and reacting the phosphorus-based flame-retardant molecule and the aconitic acid derivative to form a flame-retardant aconitic acid-derived small molecule. The flame-retardant aconitic acid-derived small molecule can then be combined with a polymer to form the flame-retardant polymer. The aconitic acid derivative can be carboxysuccinic acid, 2-(hydroxymethyl)-1,4-butenediol, or 2-(hydroxymethyl)-1,4-butanediol. The phosphorus-based flame-retardant molecule can be a phosphate-based molecule or a phosphonate-based molecule with at least one phenyl or allyl substituent. The phosphorus-based molecule can also be a thiol molecule in some embodiments. The aconitic acid derivative can be synthesized from aconitic acid obtained from a bio-based source, such as citric acid. Further embodiments are directed to an article of manufacture comprising a material that contains a flame-retardant aconitic acid-derived small molecule. The material can be a resin, adhesive, polymer, etc. Examples of polymer materials can include polyurethane, epoxies, polyhydroxyurethane, polycarbonates, polyester, polyacrylates, polyimides, polyamides, polyureas, and poly(vinyl-ester).

DETAILED DESCRIPTION

Bio-based compounds are increasingly being used in the syntheses of substances that previously required petroleum-based raw materials. One benefit of bio-based compounds is that they are from renewable resources. Therefore, these compounds have applications in sustainable, or "green," materials. Sustainable materials are becoming more and more prevalent, due to the rising costs of fossil fuels and increasing environmental regulatory controls. Advances in biotechnology have provided numerous strategies for efficiently and inexpensively producing bio-based compounds on an industrial scale.

Examples of these strategies can be found in fermentation technologies, membrane technologies, and genetic engineering. Two approaches that can use these technologies are plant-based and microorganism-based approaches. Plant-based approaches can involve obtaining a material directly from a plant, or growing plant tissues or cells that can produce bio-based compounds from various substrates using their own biosynthetic pathways. Microorganism-based approaches involve using native or genetically modified fungi, yeast, or bacteria to produce a desired compound from a structurally similar substrate.

Examples of uses for bio-based compounds include polymers, flame retardants, cross-linkers, etc. In some examples, bio-based polymers and petroleum-based polymers are blended to form a polymer composite. However, polymers can also be entirely bio-based, or produced from a combination of bio- and petroleum-based monomers. Bio-based compounds can impart flame-retardant properties to bio- and petroleum-based polymers. For example, flame-retardant cross-linkers can be incorporated into polymers, and flame-retardant monomers can be polymerized to form flame-retardant polymers. Additionally, flame-retardant small molecules can be blended with the polymers.

Aconitic acid (propene-1,2,3-tricarboxylic acid) is one example of a bio-based compound that can have applications as a component of various polymers, resins, and small molecules. Aconitic acid is an intermediate in the conversion of citrate to isocitrate during the citric acid cycle. On an industrial scale, aconitic acid is commonly obtained from fermented sugarcane extract, or synthesized from citric acid. It can be obtained from the plant- and microorganism-based bio-sources discussed above, or synthesized from petroleum-based raw materials. According to some embodiments of the present disclosure, aconitic acid is used as a precursor for flame-retardant small molecules. The aconitic acid-based flame-retardant small molecules can be added to polymers, fabrics, resins, or other materials during blending, curing, foaming, extrusion, or other processing techniques. In addition to directly adding the aconitic acid-based flame-retardant small molecules to the materials during processing, the added aconitic acid-based flame-retardant small molecules can be contained within microcapsules.

Figure 1:
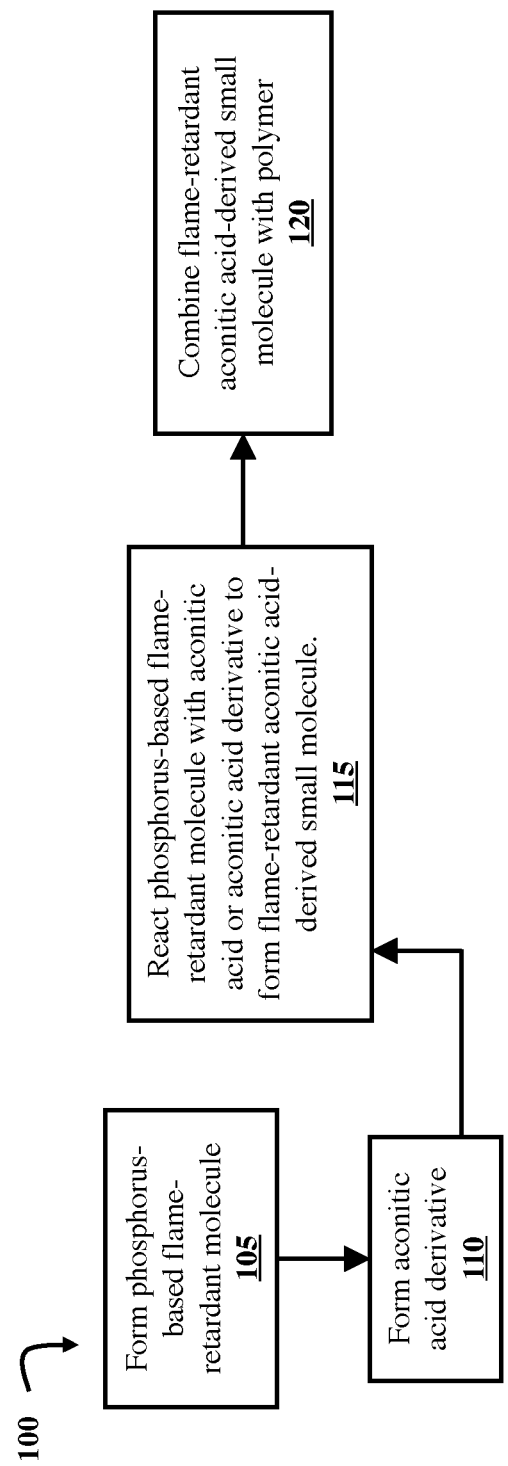
FIG. 1 is a flow diagram illustrating a process of forming a flame-retardant polymer containing a flame-retardant aconitic acid-derived small molecule, according to some embodiments of the present disclosure.

FIG. 1 is a flow diagram illustrating a process 100 of forming a flame-retardant polymer containing an aconitic acid-based flame-retardant small molecule, according to some embodiments of the present disclosure. Process 100 begins with the formation of a phosphorus-based flame-retardant molecule. This is illustrated at step 105. The phosphorus-based flame-retardant molecule has either a phosphoryl or a phosphonyl moiety (collectively referred to as an FR group) with an attached R group or phenyl (Ph) group. The R groups attached to the FR groups can vary, as is discussed in greater detail below. Examples of phosphorus-based flame-retardant molecules include phosphate- and phosphonate-based flame-retardant molecules, as well as flame-retardant thiol molecules with terminal FR groups. The structures and syntheses of phosphorus-based flame-retardant molecules are discussed in greater detail with regard to FIGS. 2 and 3A-3D.

Process 100 continues with the formation of an aconitic acid derivative. This is illustrated at step 110. Like aconitic acid, each derivative has three hydroxyl groups to which flame-retardant groups can be bound. The derivatives of aconitic acid are formed through reduction reactions involving either palladium catalysts or lithium aluminum hydride. The structures and syntheses of three examples of aconitic acid derivatives are discussed in greater detail with regard to FIG. 4. It should be noted that the formation of the aconitic derivative in step 110 is illustrated as occurring after the formation of the phosphorus-based flame-retardant molecule in step 105. However, in some embodiments, step 110 can occur before step 105.

The aconitic acid derivative and the phosphorus-based flame-retardant molecule are chemically reacted in order to form an aconitic acid-based flame-retardant small molecule. This is illustrated at step 115. The identity of the aconitic acid-derived flame retardant small molecule is determined by the aconitic acid derivative and the phosphorus-based flame-retardant molecule used in the reaction. The phosphorus-based flame-retardant molecules react with hydroxyl groups on the aconitic acid derivatives to provide the FR group with an attached R group. Examples of R groups can include allyl groups, phenyl groups, thioethers, etc. The syntheses and structures of aconitic acid-based flame-retardant small molecules, are discussed in greater detail with regard to FIGS. 5A-5F.

The aconitic acid-based flame-retardant small molecule formed in step 115 is combined with a polymer, yielding a flame-retardant polymer. This is illustrated at step 120. In some embodiments, the aconitic acid-based flame-retardant small molecule is combined with the polymer during the processing of the polymer. For example, flame-retardant aconitic acid-derived small molecules can be added to a polymer during blending, curing, foaming, or extrusion processes.

The polymer to which the aconitic acid-based flame-retardant small molecule is added can be petroleum-based, bio-based, a combination of petroleum- and bio-based, or any other synthetic or natural polymer. Examples of petroleum-based polymers that can be combined with the flame-retardant aconitic acid-derived small molecules can include epoxies, polyhydroxyurethanes, polycarbonates, polyesters, polyacrylates, polyimides, polyamides, polyureas, poly(vinyl-esters), etc. Examples of bio-based polymers that can be combined with flame-retardant aconitic acid-derived small molecules can include starch-based plastics, cellulose-based plastics, protein-based plastics, etc. Further, the aconitic acid-based flame-retardant small molecule can be added to non-polymers in some embodiments.

Figure 2:
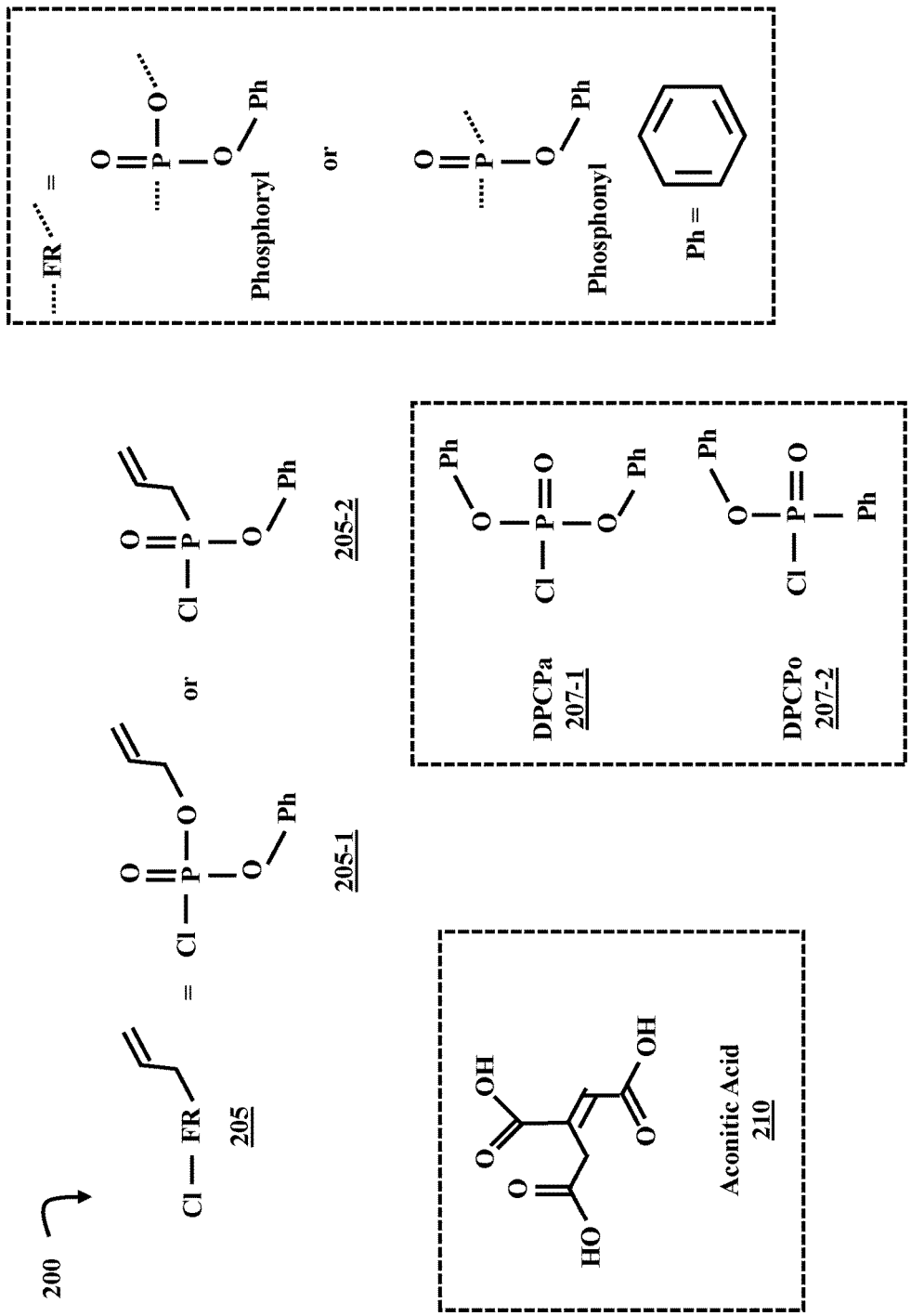
FIG. 2 is a diagrammatic representation of the molecular structures of phosphorus-based flame-retardant molecules, according to some embodiments of the present disclosure.

FIG. 2 is a diagrammatic representation of the molecular structures 200 of allyl-substituted phosphorus-based flame-retardant molecules 205-1 and 205-2 (referred to collectively as 205), phenyl-substituted flame retardant phosphorus-based flame-retardant molecules 207-1 and 207-2 (referred to collectively as 207), and aconitic acid 210, according to some embodiments of the present disclosure. Each flame-retardant phosphorus-based molecule is either a phosphate-based molecule 205-1 and 207-1 or phosphonate-based molecule 205-2 and 207-2. Herein, phosphoryl and phosphonyl moieties are replaced by the abbreviation "FR" in order to simplify illustrations of the molecular structures.

The phenyl-substituted flame-retardant phosphorus-based flame-retardant molecules, diphenyl chlorophosphate (DPCPa) 207-1 and diphenylphosphinic chloride (DPCPo) 207-

2, each have two phenyl (Ph) substituents. Each allyl-substituted phosphorus-based flame-retardant molecule 205 has a phenyl (Ph) substituent, in addition to its allyl substituent. In some embodiments, one or more phenyl groups on a phosphorus-based flame-retardant molecule are replaced by another alkyl substituent (e.g., ethyl, methyl, propyl, isopropyl, etc.). Prophetic syntheses of the allyl-substituted phosphorus-based flame-retardant molecules 205 are discussed with regard to FIGS. 3A and 3B. The phosphorus-based flame-retardant molecules 205 and 207 are reacted with the aconitic acid derivatives to form aconitic acid-based flame-retardant small molecules. These reactions are discussed in greater detail with regard to FIGS. 5A, 5C, and 5E.

Figure 3A:
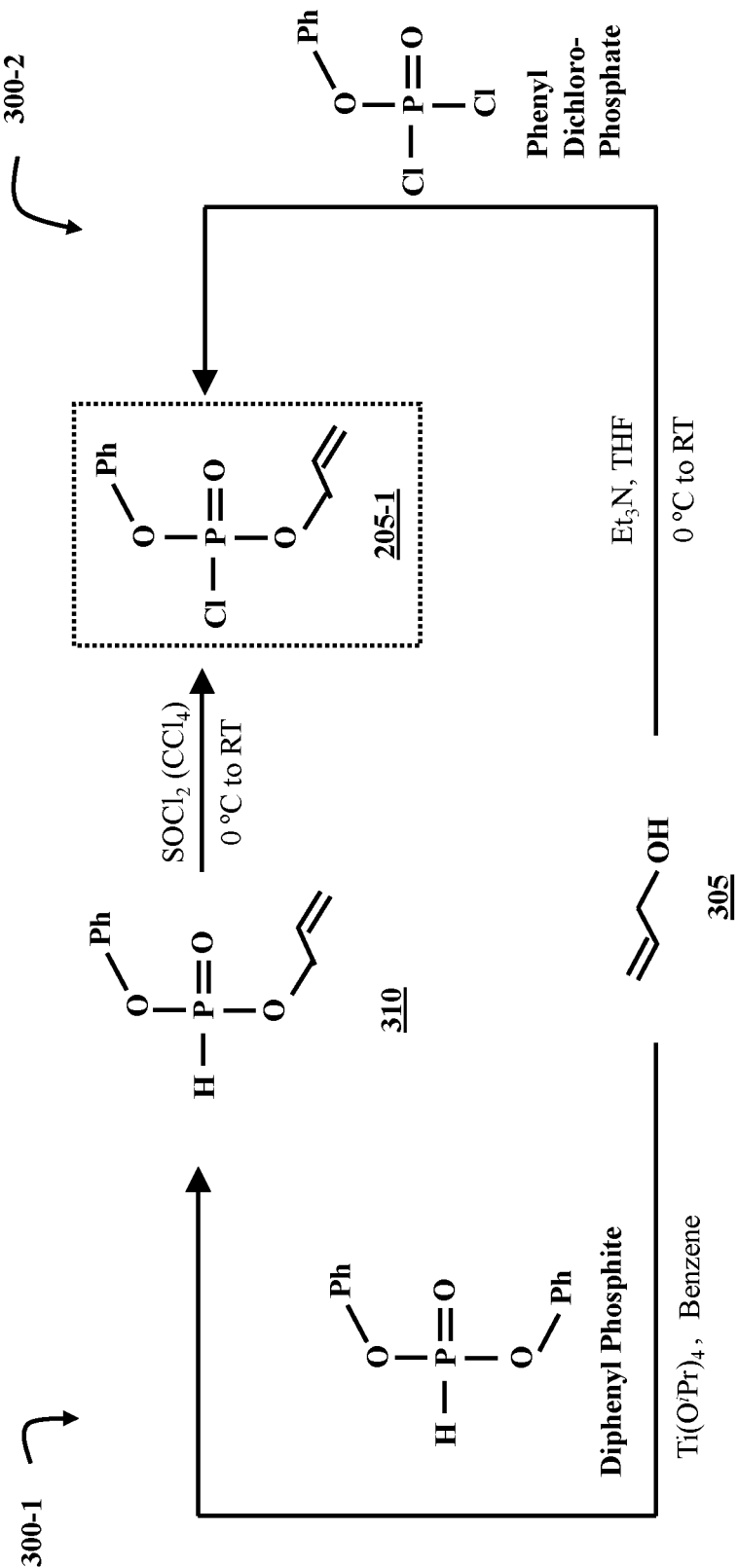
FIG. 3A is a chemical reaction diagram illustrating two processes of synthesizing a phosphate-based flame-retardant molecule, according to some embodiments of the present disclosure.

FIG. 3A is a chemical reaction diagram illustrating two processes 300-1 and 300-2 of synthesizing the phosphate-based flame-retardant molecule 205-1, according to some embodiments of the present disclosure. In both processes 300-1 and 300-2, allyl alcohol 305 is a starting material for the phosphate-based flame-retardant molecule 205-1. It should be noted that, though allyl alcohol 305 is illustrated here, other alcohols with allyl chains of varying lengths (e.g., one to twelve methylene spacer groups) can be used. Additionally, alcohols with acrylate substituents are used in some embodiments.

In process 300-1, allyl alcohol 305 is reacted with diphenyl phosphonate and titanium isopropoxide (Ti(O$^i$Pr)$_4$) in benzene to produce a precursor 310 to the phosphate-based flame-retardant molecule 205-1. In this pseudo-transesterification reaction, the precursor 310 is formed when a phenyl (Ph) substituent on diphenyl phosphite is replaced by the allyl group from the allyl alcohol 305. The precursor 310 is then reacted with thionyl chloride (SOCl$_2$) and carbon tetrachloride (CCl$_4$) over a range of 0° C. to room temperature (RT, e.g., 15-25° C.), forming the phosphate-based flame-retardant molecule 205-1. In process 300-2, the allyl alcohol 305 is reacted with phenyl dichlorophosphate in a tetrahydrofuran (THF) solution containing triethyl amine (Et$_3$N). This reaction takes place over a range of 0° C. to room temperature (RT, e.g., 15-25° C.). A chloride on the phenyl dichlorophosphate is replaced by the allyl alcohol, producing the phosphate-based flame-retardant molecule 205-1.

Figure 3B:
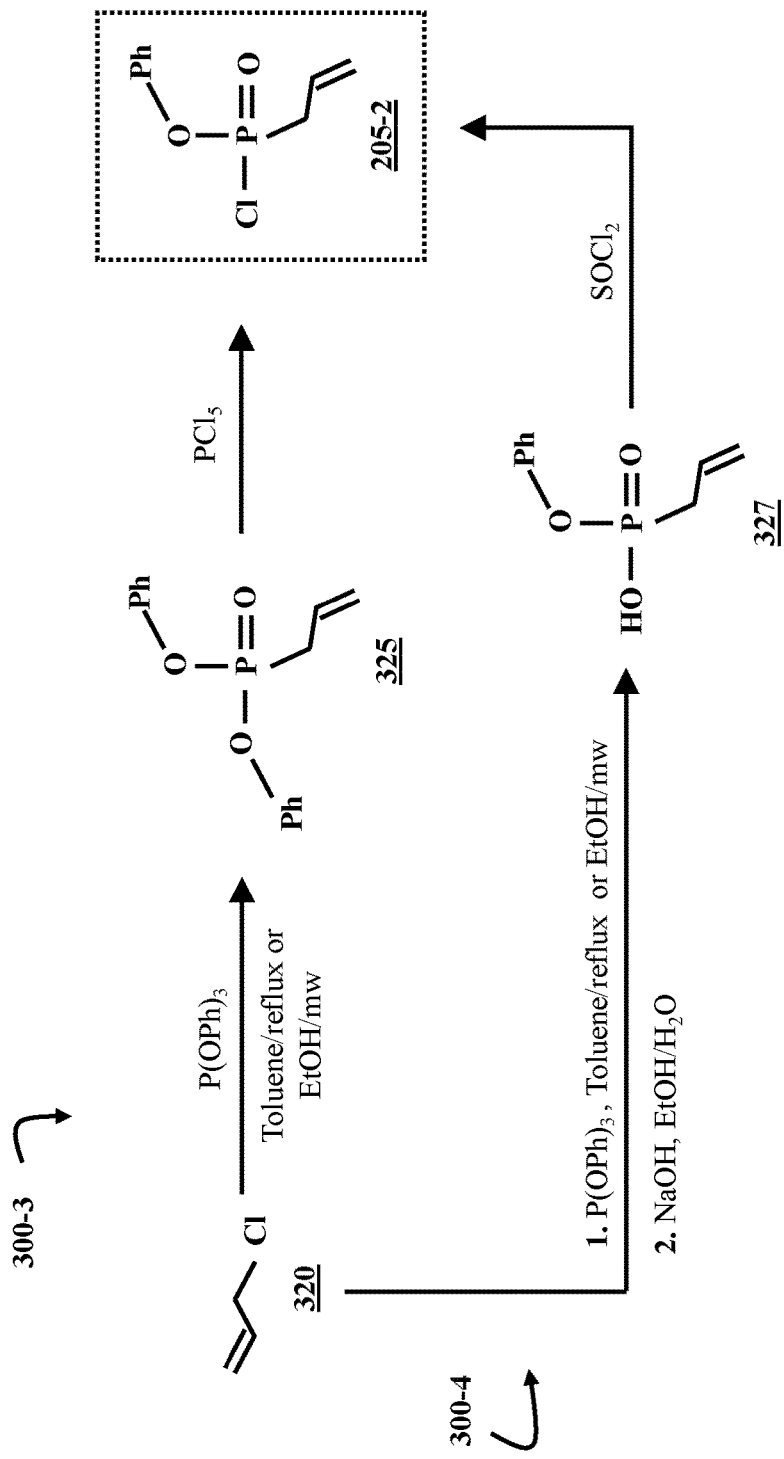
FIG. 3B is a chemical reaction diagram illustrating two processes of synthesizing a phosphonate-based flame-retardant molecule, according to some embodiments of the present disclosure.

FIG. 3B is a chemical reaction diagram illustrating two processes 300-3 and 300-4 of synthesizing the phosphonate-based flame-retardant molecule 205-2, according to some embodiments of the present disclosure. In both processes 300-3 and 300-4, allyl chloride 320 is a starting material for the phosphonate-based flame-retardant molecule 205-2. It should be noted that, as in the case of the allyl alcohol 305, organochlorides or other organohalides with allyl chains of varying lengths (e.g., one to twelve methylene spacer groups) can be used. Additionally, organochlorides with acrylate substituents are used in some embodiments.

In process 300-3, the allyl chloride 320 is reacted with triphenyl phosphite (P(OPh)$_3$). The mixture is heated, either by refluxing in toluene or microwaving (mw) in ethanol (EtOH), producing a phosphonyl ester precursor 325 to the phosphonate-based flame-retardant molecule 205-2. The phosphonyl ester precursor 325 is reacted with phosphorus pentachloride (PCl$_5$) to form the phosphonate-based flame-retardant molecule 205-2.

In process 300-4, a mixture of allyl chloride 320 and triphenyl phosphite (P(OPh)$_3$) is heated, either by refluxing in toluene or microwaving (mw) in ethanol (EtOH), producing a phenylphosphinic acid precursor 327 to the phosphonate-based flame-retardant molecule 205-2. The reaction is then quenched by raising the pH of the solution. In this prophetic example, an ethanol (EtOH)/water (H$_2$O) solution of sodium hydroxide (NaOH) is added to the reaction mixture. However, in some embodiments, bases other than sodium hydroxide, such as potassium hydroxide or lithium hydroxide, are used to quench the reaction. When the reaction has been quenched, thionyl chloride (SOCl$_2$) is added to the phenylphosphinic acid precursor 327, producing the phosphonate-based flame-retardant molecule 205-2.

Figure 3C:
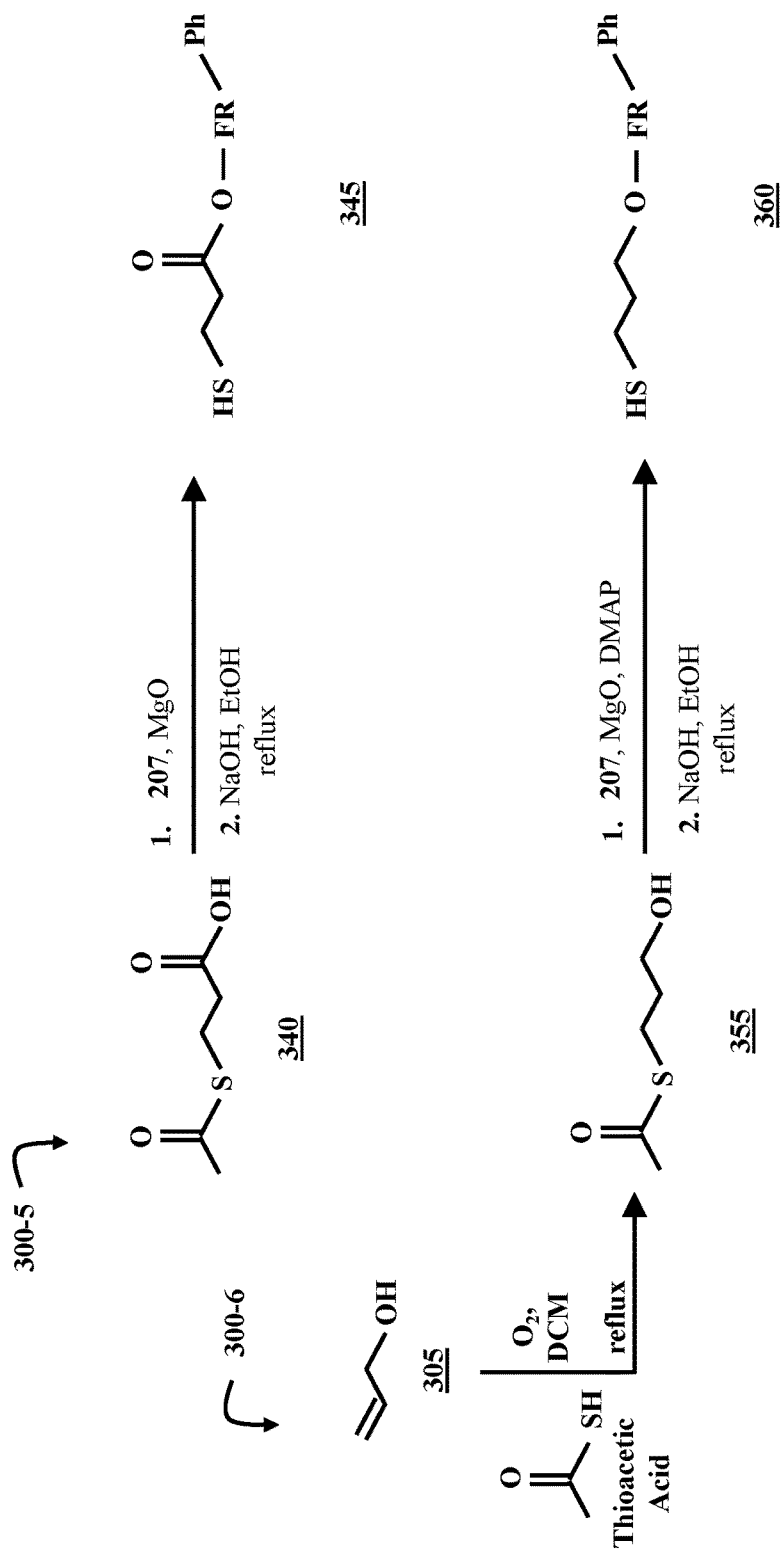
FIG. 3C is a chemical reaction diagram illustrating a process of synthesizing a carboxylic acid-derived flame-retardant thiol molecule and a process of synthesizing a hydroxy-derived flame-retardant thiol molecule, according to some embodiments of the present disclosure.

FIG. 3C is a chemical reaction diagram illustrating a process 300-5 of synthesizing a carboxylic acid-derived flame-retardant thiol molecule 345 and a process 300-6 of synthesizing a hydroxy-derived flame-retardant thiol molecule 360, according to some embodiments of the present disclosure. In process 300-5, acetate-protected thiopropionic acid 340 is reacted with magnesium oxide (MgO) and diphenyl chlorophosphate (DPCPa) 207-1 or diphenylphosphinic chloride (DPCPo) 207-2. The acetate group is then removed by refluxing the mixture in an ethanol (EtOH) solution containing sodium hydroxide (NaOH), yielding the carboxylic acid-derived flame-retardant thiol molecule 345. If the process is carried out with DPCPa 207-1, the carboxylic acid-derived flame-retardant thiol molecule 345 will have phosphoryl FR groups, and, if the reaction is carried out with DPCPo 207-2, the carboxylic acid-derived flame-retardant thiol molecule 345 will have phosphonyl FR groups.

In process 300-6, allyl alcohol 305 is reacted with thioacetic acid in a thiol-ene reaction. In the first step of the reaction, oxygen (O$_2$) is added to a dichloromethane (DCM) solution of the allyl alcohol 305 and thioacetic acid. The mixture is refluxed, resulting in an acetate-protected mercaptopropanol 355. The second step in the reaction is a substitution reaction involving diphenyl chlorophosphate (DPCPa) 207-1 and catalytic dimethylaminopyridine (DMAP) or diphenylphosphinic chloride (DPCPo) 207-2. The acetate group is removed by refluxing the mixture in an ethanol (EtOH) solution containing sodium hydroxide (NaOH). This step results in the production of the hydroxy-derived flame-retardant thiol molecule 360. If the process is carried out with DPCPa 207-1, the hydroxy-derived flame-retardant thiol molecule 360 will have phosphoryl FR groups, and, if the reaction is carried out with DPCPo 207-2, the hydroxy-derived flame-retardant thiol molecule 360 will have phosphonyl FR groups.

Figure 3D:
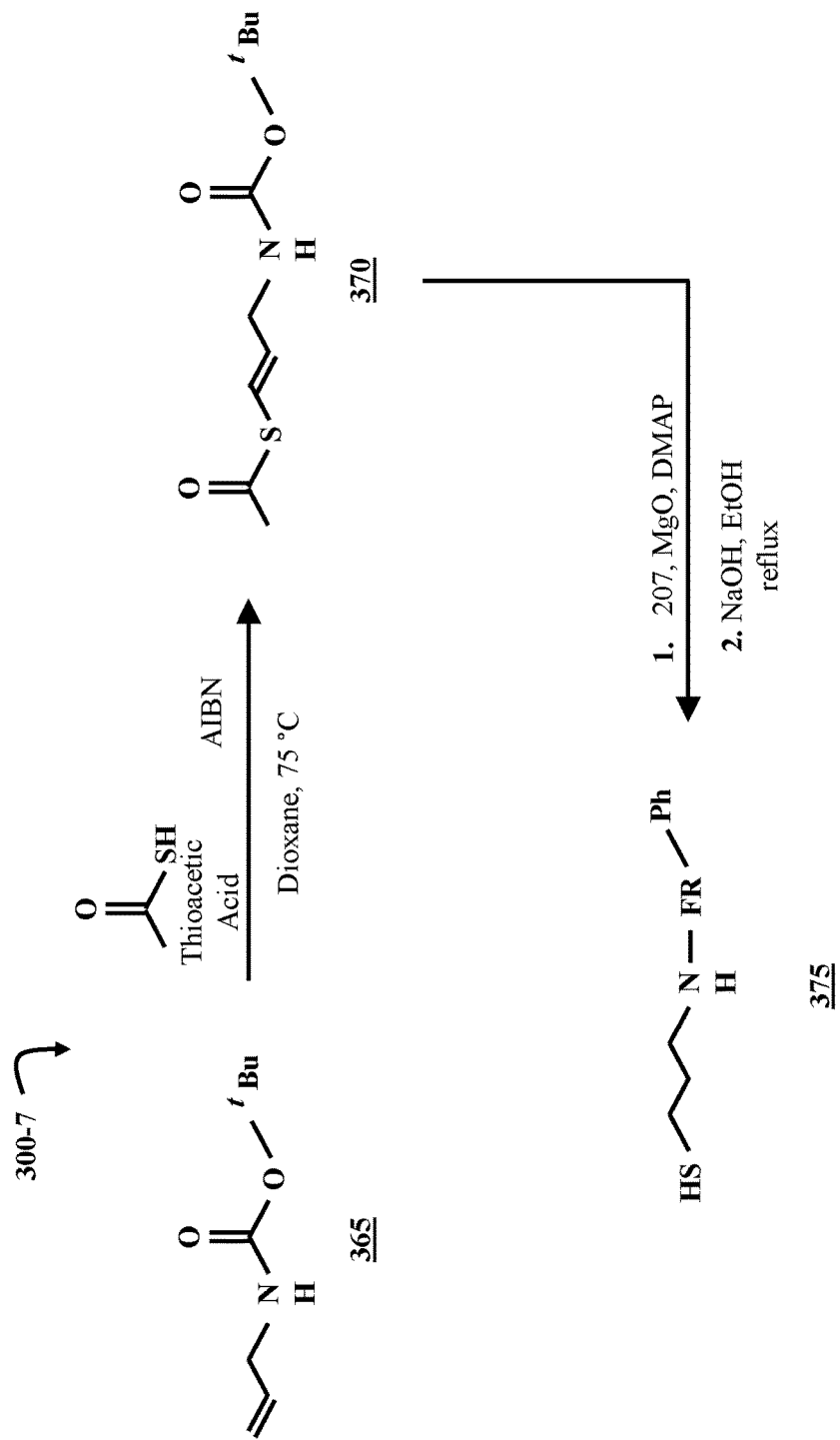
FIG. 3D is a chemical reaction diagram illustrating a process of synthesizing an amino-derived flame-retardant thiol molecule, according to some embodiments of the present disclosure.

FIG. 3D is a chemical reaction diagram illustrating a process 300-7 of synthesizing an amino-derived flame-retardant thiol molecule 375, according to some embodiments of the present disclosure. In process 300-7, 1-(boc-amino)-3-butene 365 is first reacted with thioacetic acid in a thiol-ene reaction. Azobisisobutyronitrile (AIBN) is added to the dioxane solution of 1-(boc-amino)-3-butene 365 and thioacetic acid, and the mixture is stirred at 75° C., resulting in an acetate-protected precursor 370 to the amino-derived flame-retardant thiol molecule 375. The second step in process 300-7 is a substitution reaction with diphenyl chlorophosphate (DPCPa) 207-1 or diphenylphosphinic chloride (DPCPo) and catalytic dimethylaminopyridine (DMAP). The acetate group and boc groups are removed under basic conditions (e.g., by refluxing the mixture in an ethanol (EtOH) solution containing sodium hydroxide (NaOH)). This step results in the production of the amino-derived flame-retardant thiol molecule 375. If the process is carried out with DPCPa 207-1, the amino-derived flame-retardant thiol molecule 375 will have phosphoryl FR groups, and, if the reaction is carried out with DPCPo 207-2, the amino-derived flame-retardant thiol molecule 375 will have phosphonyl FR groups.

Figure 4:
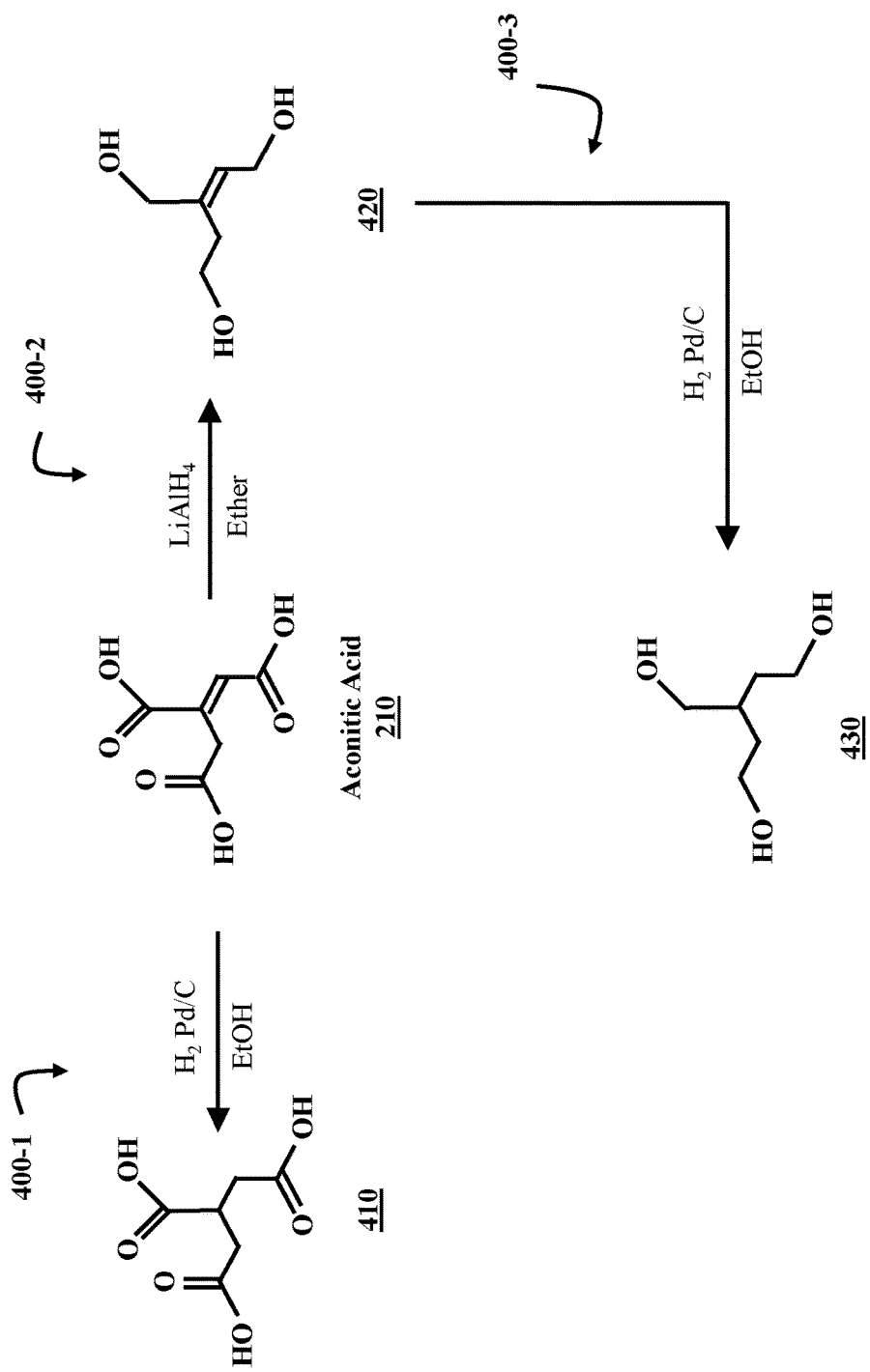
FIG. 4 is a chemical reaction diagram illustrating processes of synthesizing three aconitic acid derivatives, according to some embodiments of the present disclosure.

FIG. 4 is a chemical reaction diagram illustrating processes 400-1, 400-2, and 400-3 of synthesizing three derivatives of aconitic acid 210, according to some embodiments of the present disclosure. The three aconitic acid derivatives are carboxysuccinic acid 410, a butenetriol 420 (2-(hydroxymethyl)-1,4-butenediol), and a butanetriol 430 (2-(hydroxymethyl)-1,4-butanediol). These aconitic acid derivatives are precursors for the flame-retardant aconitic acid-derived small molecules, as is described in greater detail with regard to FIGS. 5A-5H.

In process 400-1, aconitic acid 210 is reduced in an ethanol solution. The reduction is carried out with hydrogen gas ($H_2$) and a palladium on carbon (Pd/C) catalyst, and produces the aconitic acid derivative, carboxysuccinic acid 410. In process 400-2, aconitic acid 210 is reduced by lithium aluminum hydride ($LiAlH_4$) in ether ($Et_2O$), producing the butenetriol 420. In process 400-3, the butenetriol 420 is reduced under the same conditions as aconitic acid 210 in process 400-1, producing the butanetriol 430. Though FIG. 4 illustrates processes 400-1, 400-2, and 400-3 as involving the reducing agents $LiAlH_4$ and $H_2$ with Pd/C, other reducing agents can be used (e.g., sodium borohydride ($NaBH_4$), carbon monoxide (CO), iron(II) compounds, etc.). In addition, in some embodiments, carboxysuccinic acid 410, butenetriol 420, and butanetriol 430 are obtained from commercial sources.

Figure 5A:
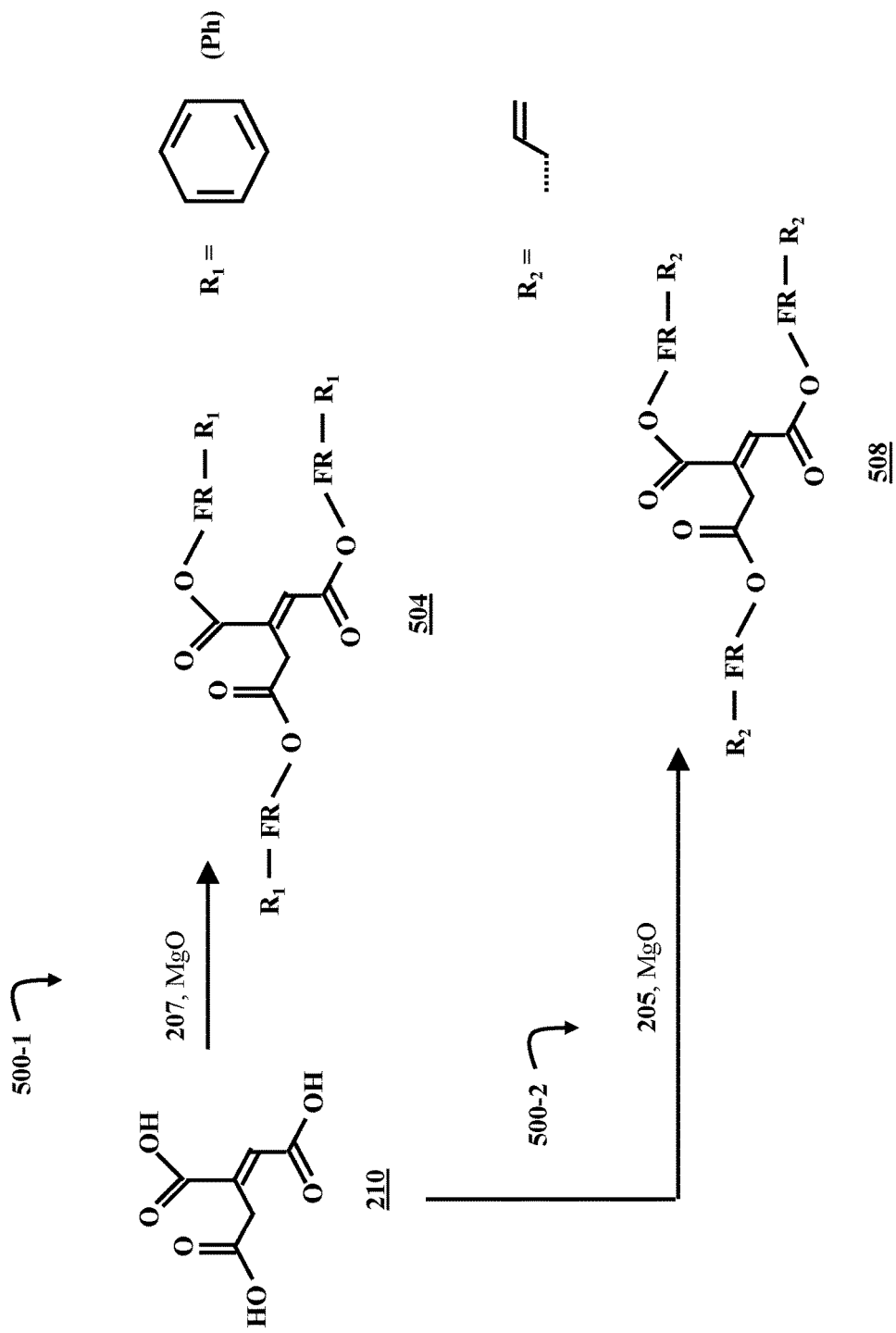
FIG. 5A is a chemical reaction diagram illustrating a process of synthesizing a phenyl-substituted flame-retardant aconitic acid-derived small molecule and a process of forming an allyl-substituted flame-retardant aconitic acid-derived small molecule, according to some embodiments of the present disclosure.

FIG. 5A is a chemical reaction diagram illustrating a process 500-1 of synthesizing a phenyl ($R_1$)-substituted flame-retardant aconitic acid-derived small molecule 504 and a process 500-2 of forming an allyl ($R_2$)-substituted flame-retardant aconitic acid-derived small molecule 508, according to some embodiments of the present disclosure. In process 500-1, aconitic acid 210 is combined with either diphenyl chlorophosphate (DPCPa) 207-1 or diphenylphosphinic chloride (DPCPo) 207-2. Magnesium oxide (MgO) is added to the reaction mixture, producing the phenyl-substituted flame-retardant aconitic acid-derived small molecule 504. If the reaction is carried out with DPCPa 207-1, the phenyl-substituted flame-retardant aconitic acid-derived small molecule 504 will have a phosphoryl FR group, and, if the reaction is carried out with the DPCPo 207-2, the phenyl-substituted flame-retardant aconitic acid-derived small molecule 504 will have a phosphonyl FR group.

In process 500-2, the aconitic acid 210 is reacted with a phosphorus-based flame-retardant molecule 205 and catalytic dimethylaminopyridine (DMAP) in a dichloromethane (DCM) solution. It should be noted that, in some embodiments of the reactions discussed herein that involve DMAP, stoichiometric triethylamine is used instead of DMAP. The reaction between the aconitic acid 210 and the phosphate-based flame-retardant molecule 205 produces an allyl-substituted flame-retardant aconitic acid-derived small molecule 508. If the reaction is carried out with the phosphate-based flame-retardant molecule 205-1, the allyl-substituted flame-retardant aconitic acid-derived small molecule 508 will have phosphoryl FR groups, and, if the reaction is carried out with the phosphonate-based flame-retardant molecule 205-2, the allyl-substituted flame-retardant aconitic acid-derived small molecule 508 will have phosphonyl FR groups.

Figure 5B:
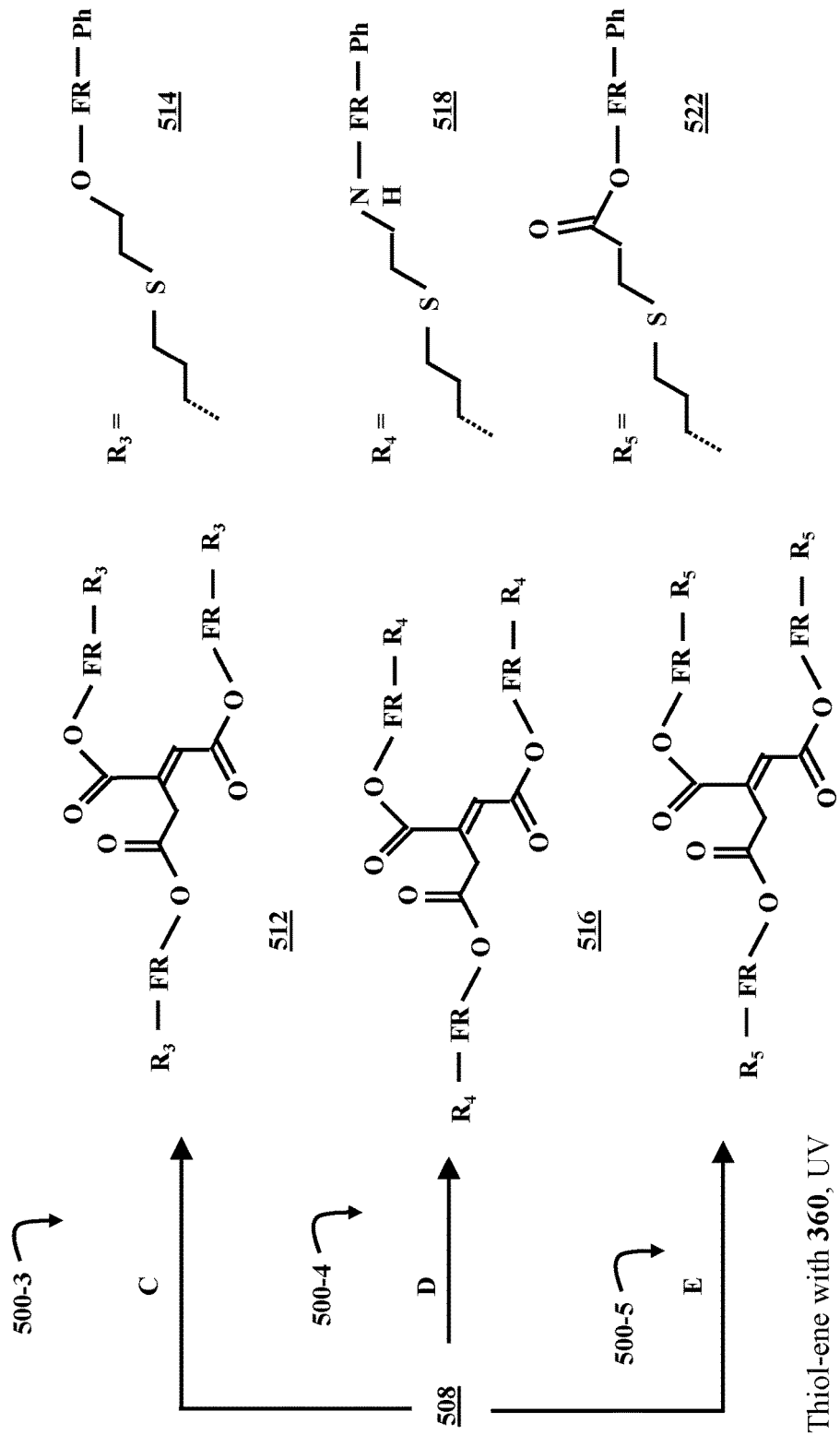
FIG. 5B is a chemical reaction diagram illustrating three processes of synthesizing thioether-linked flame-retardant aconitic acid-derived small molecules, according to some embodiments of the present disclosure.

FIG. 5B is a chemical reaction diagram illustrating three processes 500-3, 500-4, and 500-5 of synthesizing thioether-linked flame-retardant aconitic acid-derived small molecules, according to some embodiments of the present disclosure. Each process is a thiol-ene reaction between the allyl-substituted flame-retardant aconitic acid-derived small molecule 508 and a flame-retardant thiol molecule 345, 360, or 375. The syntheses and structures of the flame-retardant thiol molecules are discussed in greater detail with regard to FIGS. 3C and 3D.

In process 500-3, the allyl-substituted flame-retardant aconitic acid-derived small molecule 508 is reacted with the hydroxy-derived flame-retardant thiol molecule 360 under UV light. The resulting thioether-linked flame-retardant aconitic acid-derived small molecule 512 has a thioether $R_3$ group 514 that corresponds to the hydroxy-derived flame-retardant thiol molecule 360. In process 500-4, the allyl-substituted flame-retardant aconitic acid-derived small molecule 508 is reacted with the amino-derived flame-retardant thiol molecule 375 in a methanol (MeOH) solution under UV light. The resulting thioether-linked flame-retardant aconitic acid-derived small molecule 516 has a thioether $R_4$ group 518 that corresponds to the amino-derived flame-retardant thiol molecule 375. In process 500-5, the allyl-substituted flame-retardant carboxysuccinic acid-derived small molecule 510 is reacted with the carboxylic acid-derived flame-retardant thiol molecule 345 under UV light in a pH 9 methanol (MeOH) solution. The resulting thioether-linked flame-retardant aconitic acid-derived small molecule 520 has a thioether $R_5$ group 522 that corresponds to the carboxylic acid-derived flame-retardant thiol molecule 345.

Figure 5C:
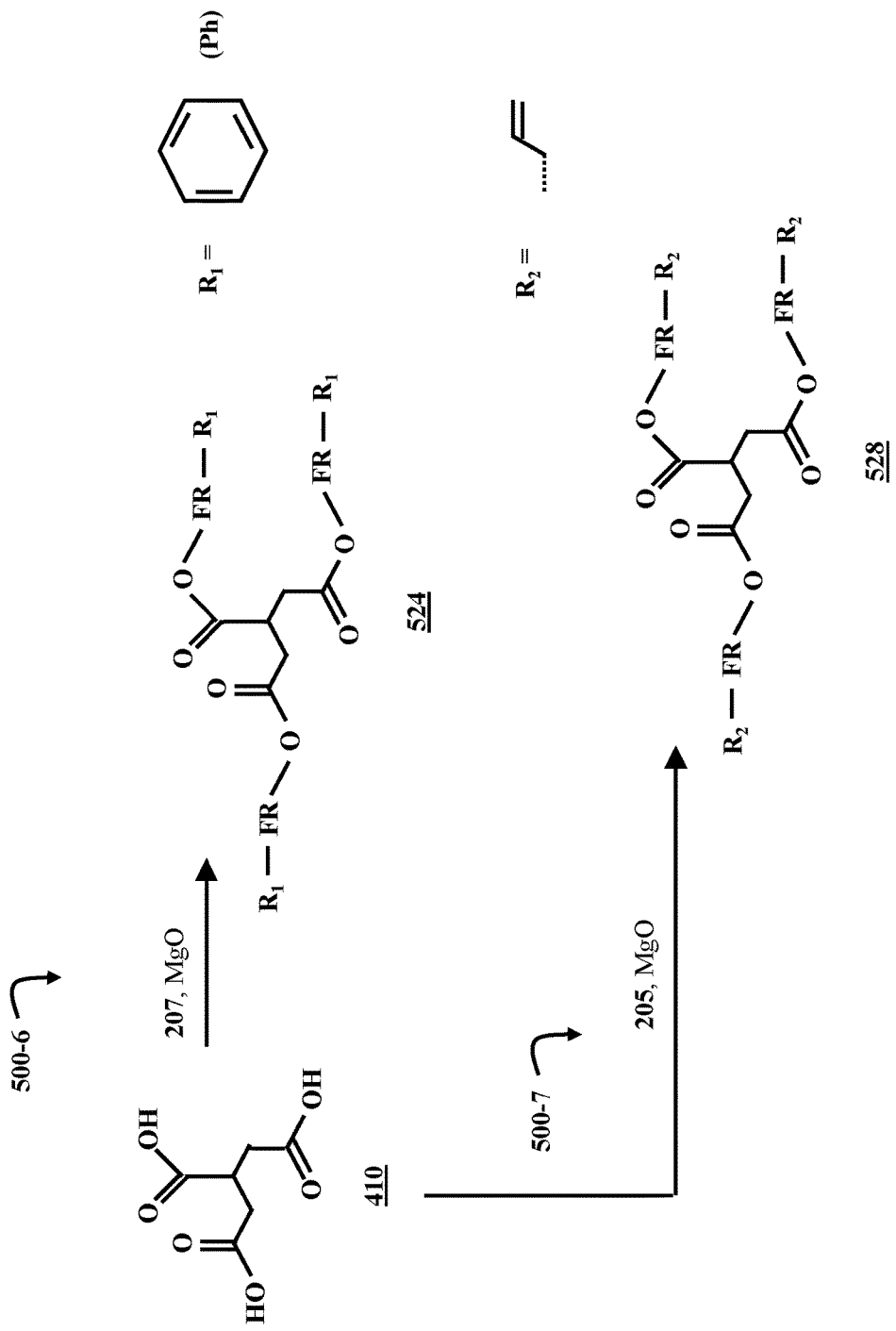
FIG. 5C is a chemical reaction diagram illustrating a process of synthesizing a phenyl-substituted flame-retardant carboxysuccinic acid-derived small molecule and a process of forming an allyl-substituted flame-retardant carboxysuccinic acid-derived small molecule, according to some embodiments of the present disclosure.

FIG. 5C is a chemical reaction diagram illustrating a process 500-6 of synthesizing a phenyl ($R_1$)-substituted flame-retardant carboxysuccinic acid-derived small molecule 524 and a process 500-7 of forming an allyl ($R_2$)-substituted flame-retardant carboxysuccinic acid-derived small molecule 528, according to some embodiments of the present disclosure. In process 500-6, the carboxysuccinic acid 410 is reacted with either diphenyl chlorophosphate (DPCPa) 207-1 or diphenylphosphinic chloride (DPCPo) 207-2. Magnesium oxide (MgO) is added to the reaction mixture. The mixture is then refluxed with catalytic dimethylaminopyridine (DMAP) in a dichloromethane (DCM) solution, producing the phenyl-substituted flame-retardant carboxysuccinic acid-derived small molecule 505. If the process is carried out with DPCPa 207-1, the phenyl-substituted carboxysuccinic acid-derived small molecule 524 will have phosphoryl FR groups, and, if the reaction is carried out with DPCPo 207-2, the phenyl-substituted carboxysuccinic acid-derived small molecule 524 will have phosphonyl FR groups.

In process 500-7, the carboxysuccinic acid 410 is reacted with a phosphorus-based flame-retardant molecule 205 and catalytic dimethylaminopyridine (DMAP) in a dichloromethane (DCM) solution. The reaction between the carboxysuccinic acid 410 and the phosphate-based flame-retardant molecule 205 produces an allyl-substituted flame-retardant carboxysuccinic acid-derived small molecule 528. If the reaction is carried out with the phosphate-based flame-retardant molecule 205-1, the allyl-substituted flame-retardant carboxysuccinic acid-derived small molecule 528 will have phosphoryl FR groups, and, if the reaction is carried out with the phosphonate-based flame-retardant molecule 205-2, the allyl-substituted flame-retardant carboxysuccinic acid-derived small molecule 528 will have phosphonyl FR groups.

Figure 5D:
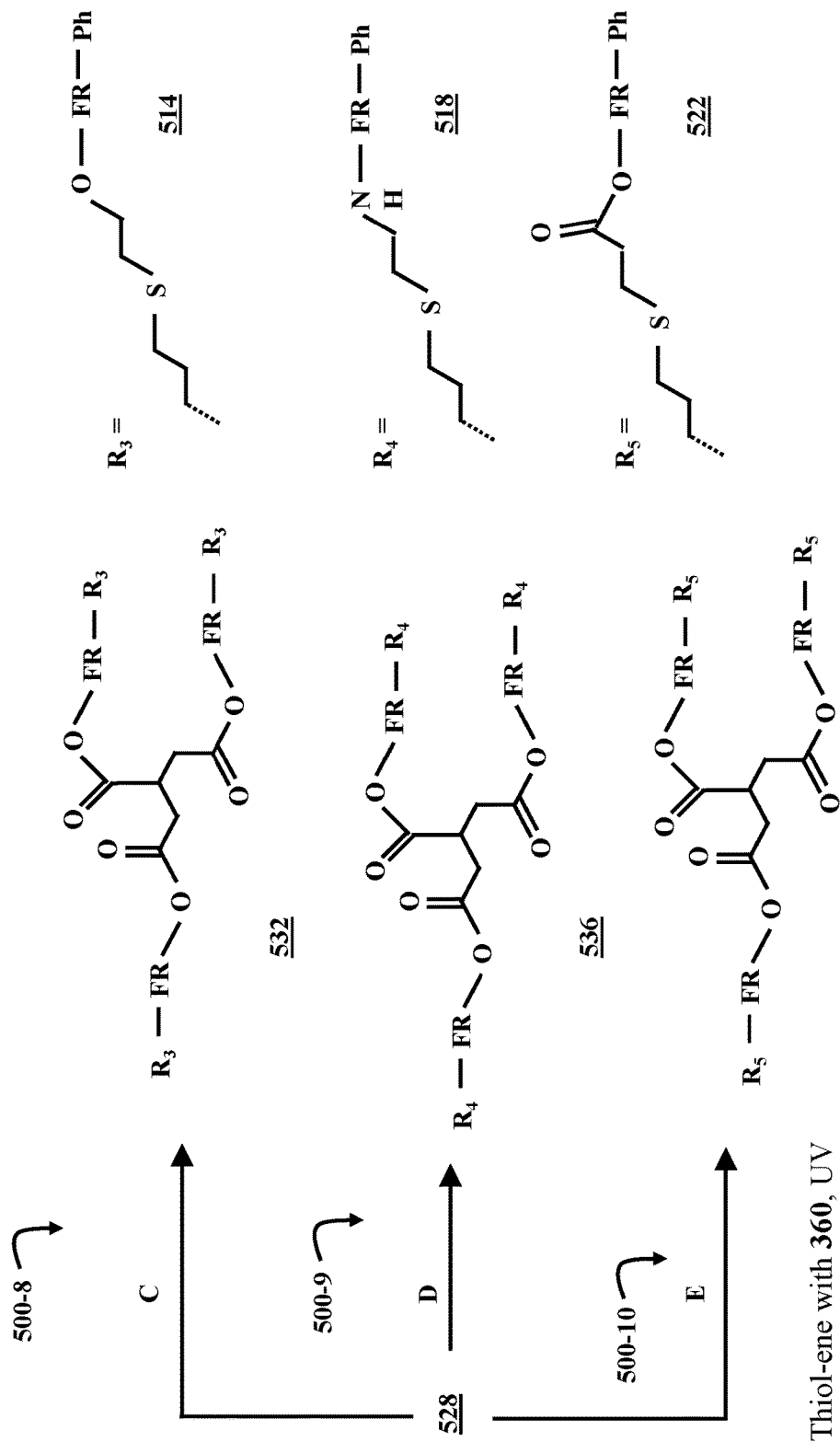
FIG. 5D is a chemical reaction diagram illustrating three processes of synthesizing thioether-linked flame-retardant carboxysuccinic acid-derived small molecules, according to some embodiments of the present disclosure.

FIG. 5D is a chemical reaction diagram illustrating three processes 500-8, 500-9, and 500-10 of synthesizing thioether-linked flame-retardant carboxysuccinic acid-derived small molecules, according to some embodiments of the present disclosure. Each process is a thiol-ene reaction between the allyl-substituted flame-retardant carboxysuccinic acid-derived small molecule 528 and a flame-retardant thiol molecule 345, 360, or 375. The syntheses and structures of the flame-retardant thiol molecules are discussed in greater detail with regard to FIGS. 3C and 3D.

In process 500-8, the allyl-substituted flame-retardant carboxysuccinic acid-derived small molecule 528 is reacted with the hydroxy-derived flame-retardant thiol molecule 360 under UV light. The resulting thioether-linked flame-retardant carboxysuccinic acid-derived small molecule 532 has a thioether $R_3$ group 514 that corresponds to the hydroxy-derived flame-retardant thiol molecule 360. In process 500-9, the allyl-substituted flame-retardant carboxysuccinic acid-derived small molecule 528 is reacted with the amino-derived flame-retardant thiol molecule 375 in a methanol (MeOH) solution under UV light. The resulting thioether-linked flame-retardant carboxysuccinic acid-derived small molecule 536 has a thioether $R_4$ group 518 that corresponds to the amino-derived flame-retardant thiol molecule 375. In process 500-10, the allyl-substituted flame-retardant carboxysuccinic acid-derived small molecule 528 is reacted with the carboxylic acid-derived flame-retardant thiol molecule 345 under UV light in a pH 9 methanol (MeOH) solution. The resulting thioether-linked flame-retardant phenol derivative 540 has a thioether $R_5$ group 522 that corresponds to the carboxylic acid-derived flame-retardant thiol molecule 345.

Figure 5E:
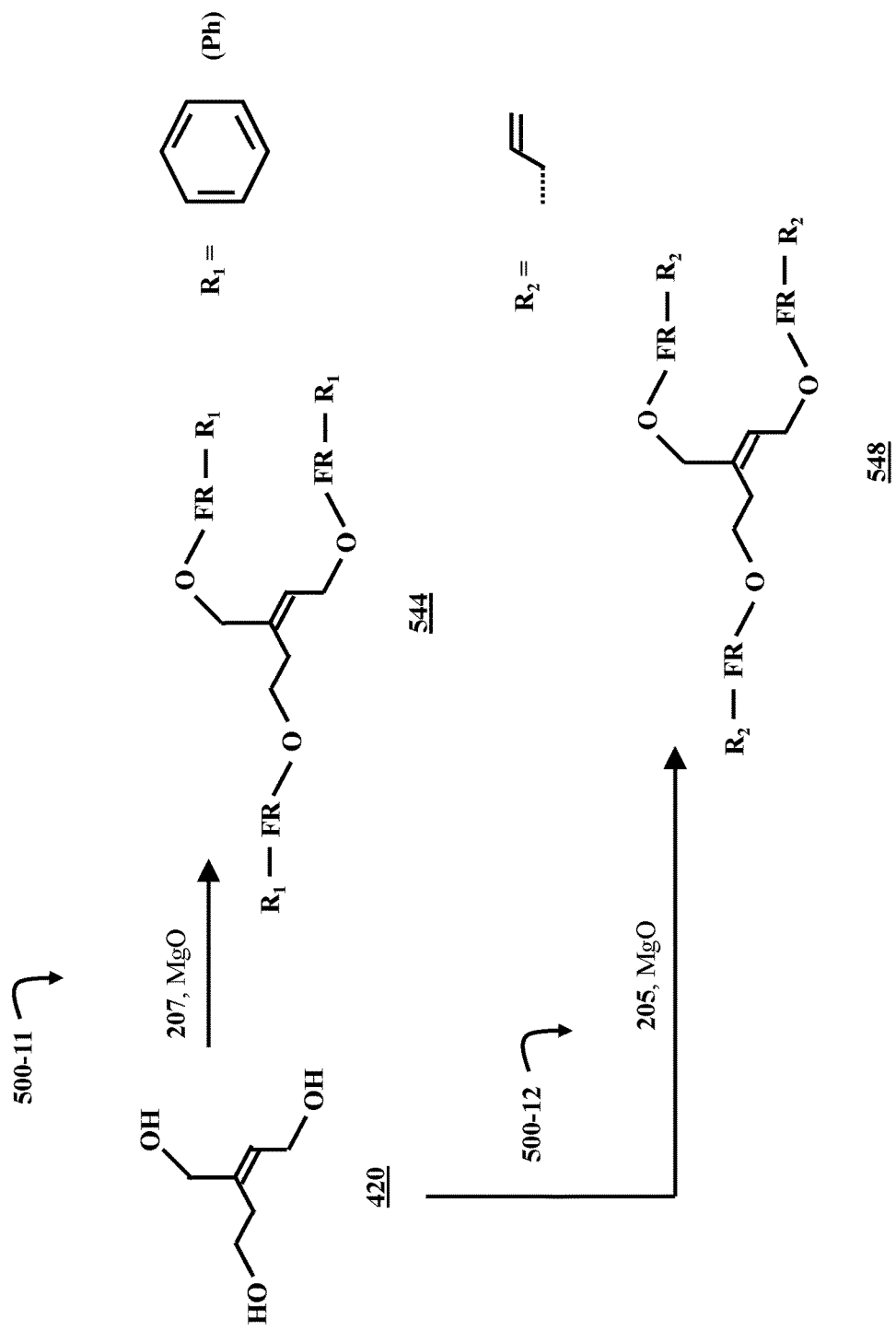
FIG. 5E is a chemical reaction diagram illustrating a process of synthesizing a phenyl-substituted flame-retardant butenetriol-derived small molecule and a process of forming an allyl-substituted flame-retardant butenetriol-derived small molecule, according to some embodiments of the present disclosure.

FIG. 5E is a chemical reaction diagram illustrating a process 500-11 of synthesizing a phenyl ($R_1$)-substituted flame-retardant butenetriol-derived small molecule 544 and a process 500-12 of forming an allyl ($R_2$)-substituted flame-retardant butenetriol-derived small molecule 548, according to some embodiments of the present disclosure. In process 500-11, the butenetriol 420 is reacted with either diphenyl chlorophosphate (DPCPa) 207-1 or diphenylphosphinic chloride (DPCPo) 207-2. Magnesium oxide (MgO) is added to the reaction mixture. The mixture is then refluxed with catalytic dimethylaminopyridine (DMAP) in a dichloromethane (DCM) solution, producing the phenyl-substituted flame-retardant butenetriol-derived small molecule 544. If process 500-6 is carried out with DPCPa 207-1, the phenyl-substituted flame-retardant butenetriol-derived small molecule 544 will have phosphoryl FR groups, and, if the reaction is carried out with DPCPo 207-2, the phenyl-substituted flame-retardant butenetriol-derived small molecule 544 will have phosphonyl FR groups.

In process 500-12, the butenetriol 420 is combined with a phosphorus-based flame-retardant molecule 205 in a dichloromethane (DCM) solution. Magnesium oxide (MgO) is then added to the solution, and the mixture is refluxed with catalytic DMAP. The reaction between the butenetriol 420 and the phosphorus-based flame-retardant molecule 205 produces the allyl-substituted flame-retardant butenetriol-derived small molecule 548. If the reaction is carried out with the phosphate-based flame-retardant molecule 205-1, the allyl-substituted flame-retardant butenetriol-derived small molecule 548 will have phosphoryl FR groups, and, if the reaction is carried out with the phosphonate-based flame-retardant molecule 205-2, the allyl-substituted flame-retardant butenetriol-derived small molecule 548 will have phosphonyl FR groups.

Figure 5F:
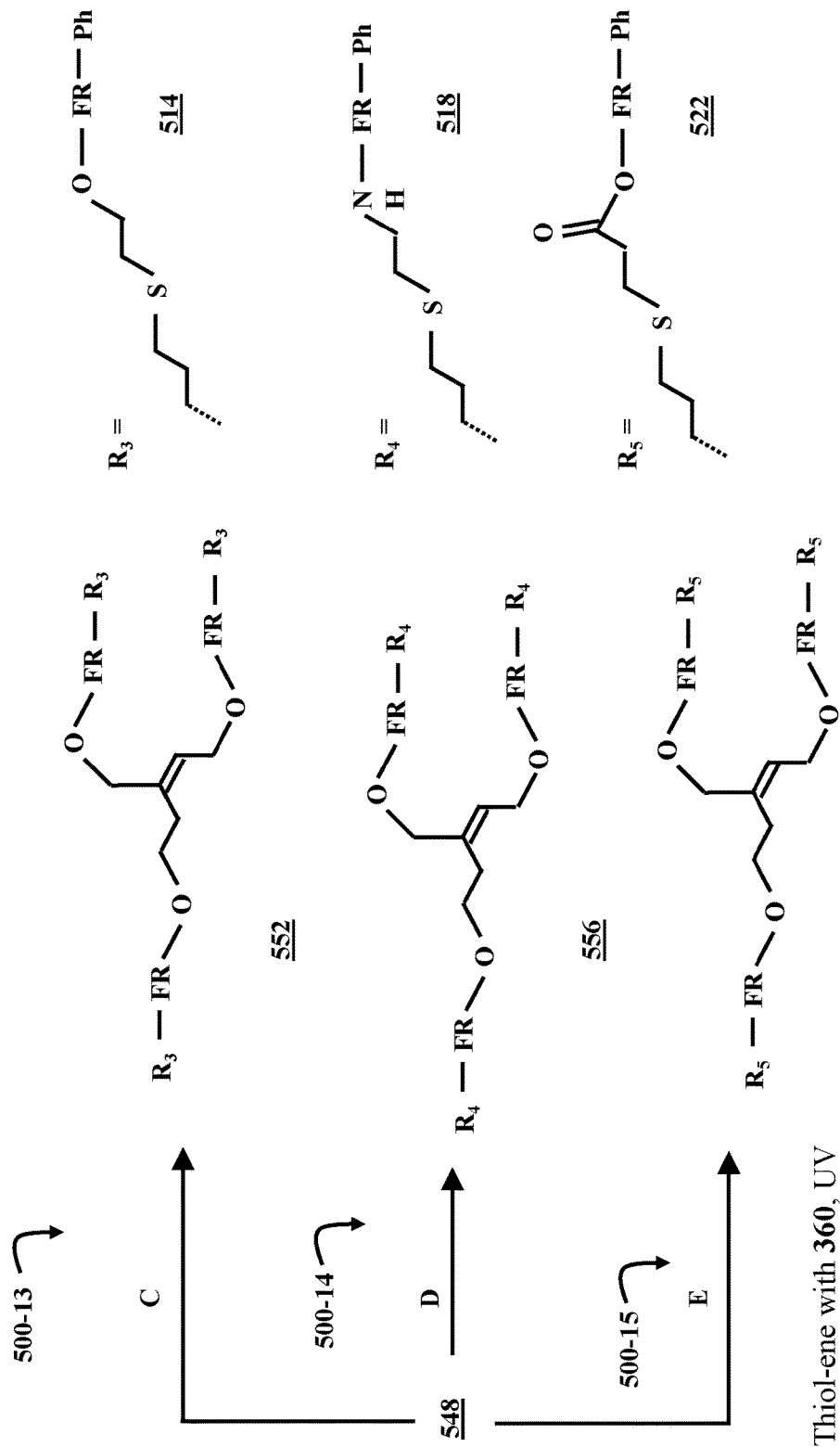
FIG. 5F is a chemical reaction diagram illustrating three processes of synthesizing thioether-linked flame-retardant butenetriol-derived small molecules, according to some embodiments of the present disclosure.

FIG. 5F is a chemical reaction diagram illustrating three processes 500-13, 500-14, and 500-15 of synthesizing thioether-linked flame-retardant butenetriol-derived small molecules, according to some embodiments of the present disclosure. Each process is a thiol-ene reaction between the allyl-substituted flame-retardant butenetriol-derived small molecule 548 and a flame-retardant thiol molecule 345, 360, 375. The syntheses and structures of the flame-retardant thiol molecules are discussed in greater detail with regard to FIGS. 3C and 3D.

In process 500-13, the allyl-substituted flame-retardant butenetriol-derived small molecule 548 is reacted with the hydroxy-derived flame-retardant thiol molecule 360 under UV light. The resulting thioether-linked flame-retardant butenetriol-derived small molecule 552 has an $R_3$ group 514 that corresponds to the hydroxy-derived flame-retardant thiol molecule 360. In process 500-14, the allyl-substituted flame-retardant butenetriol-derived small molecule 548 is reacted with the amino-derived flame-retardant thiol molecule 375 in a methanol (MeOH) solution under UV light. The resulting thioether-linked flame-retardant butenetriol-derived small molecule 556 has an $R_4$ group 518 corresponding to the amino-derived flame-retardant thiol molecule 375. In process 500-15, the allyl-substituted flame-retardant butenetriol-derived small molecule 548 is reacted with the carboxylic acid-derived flame-retardant thiol molecule 345 under UV light in a pH 9 methanol (MeOH) solution. The resulting thioether-linked flame-retardant butenetriol-derived small molecule 560 has an $R_5$ group 522 corresponding to the carboxylic acid-derived flame-retardant thiol molecule 345.

Figure 5G:
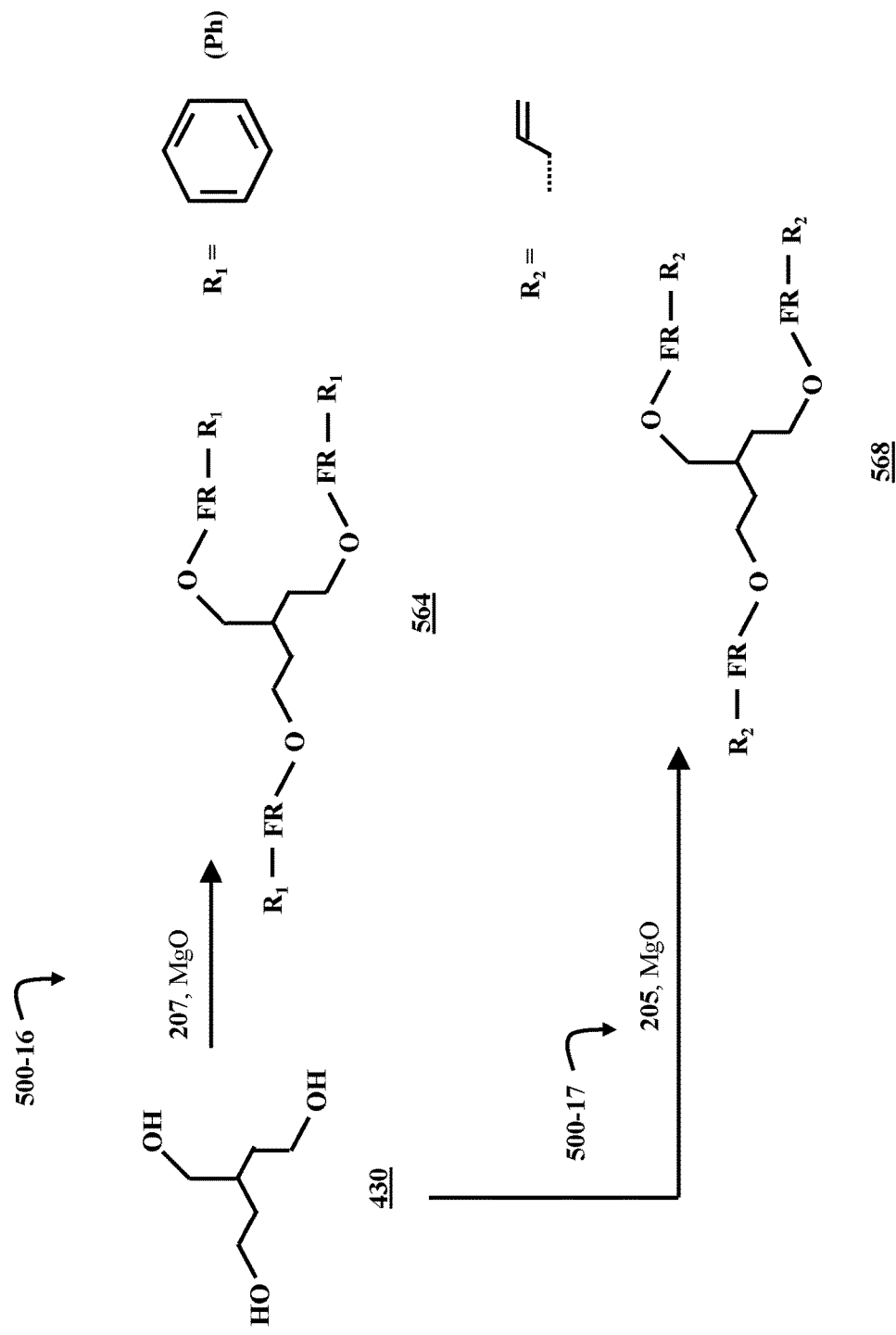
FIG. 5G is a chemical reaction diagram illustrating a process of synthesizing a phenyl-substituted flame-retardant butanetriol-derived small molecule and a process of forming an allyl-substituted benzyl alcohol flame-retardant butanetriol-derived small molecule, according to some embodiments of the present disclosure.

FIG. 5G is a chemical reaction diagram illustrating a process 500-16 of synthesizing a phenyl ($R_1$)-substituted flame-retardant butanetriol-derived small molecule 564 and a process 500-17 of forming an allyl ($R_2$)-substituted flame-retardant butanetriol-derived small molecule 568, according to some embodiments of the present disclosure. In process 500-16, the butanetriol 430 is reacted with either diphenyl chlorophosphate (DPCPa) 207-1 or diphenylphosphinic chloride (DPCPo) 207-2. Magnesium oxide (MgO) is added to the reaction mixture. The mixture is refluxed with catalytic dimethylaminopyridine (DMAP) in a dichloromethane (DCM) solution, producing the phenyl-substituted flame-retardant butanetriol-derived small molecule 564. If the reaction is carried out with DPCPa 207-1, the phenyl-substituted flame-retardant butanetriol-derived small molecule 564 will have phosphoryl FR groups, and, if the reaction is carried out with DPCPo 207-2, the phenyl-substituted flame-retardant butanetriol-derived small molecule 564 will have phosphonyl FR groups.

Process 500-17 produces an allyl-substituted flame-retardant butanetriol-derived small molecule 568. The butanetriol 430 is reacted with a phosphorus-based flame-retardant molecule 205 and magnesium oxide (MgO). The reaction between the butanetriol 430 and the phosphorus-based flame-retardant molecule 205 produces the allyl-substituted flame-retardant butanetriol-derived small molecule 568. As in the case of the flame-retardant aconitic acid-derived small molecule 508, if the reaction is carried out with the phosphate-based flame-retardant molecule 205-1, the allyl-substituted flame-retardant butanetriol-derived small molecule 568 will have phosphoryl FR groups, and, if the reaction is carried out with the phosphonate-based flame-retardant molecule 205-2, the allyl-substituted flame-retardant butanetriol-derived small molecule 568 will have phosphonyl FR groups.

Figure 5H:
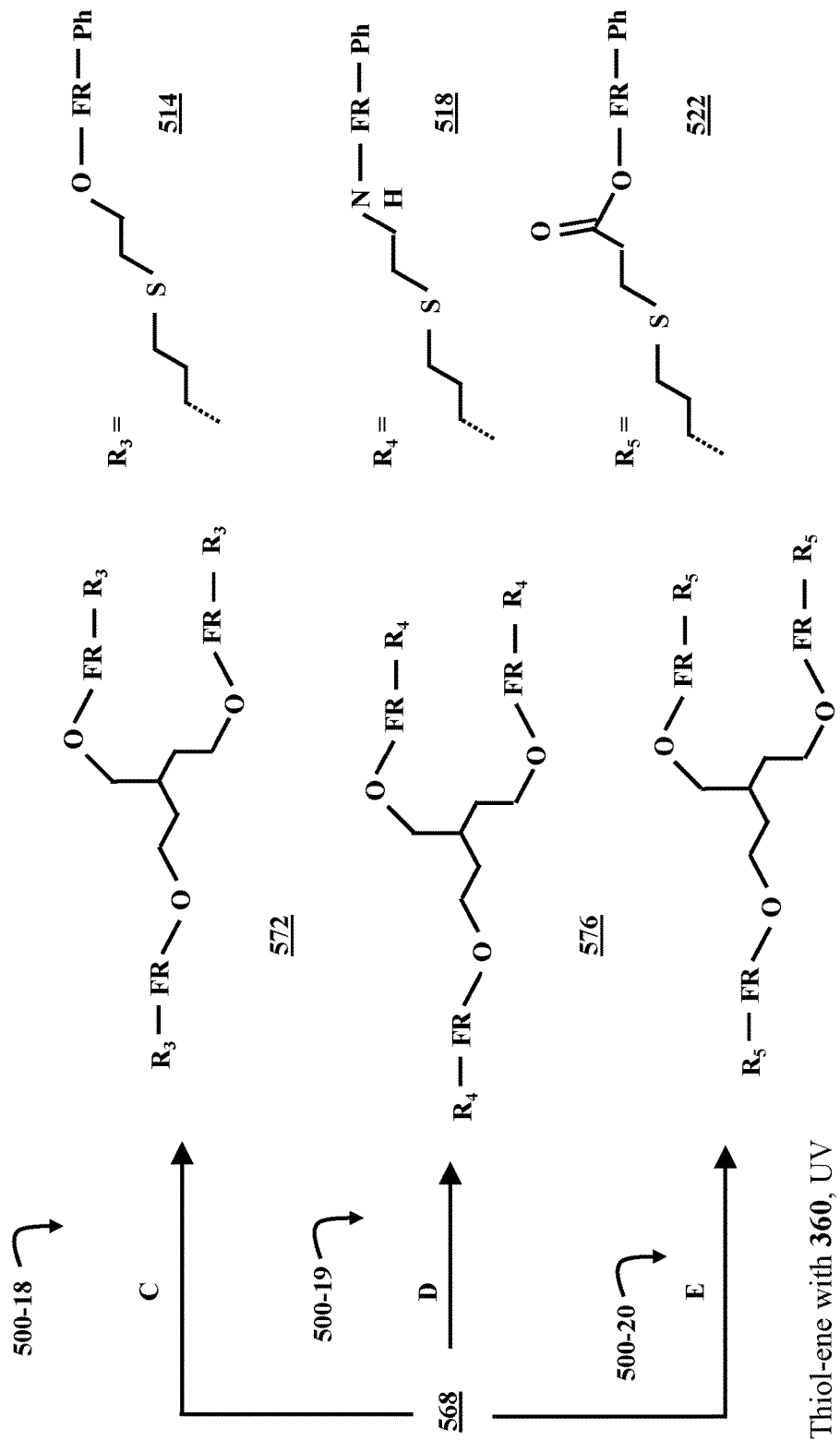
FIG. 5H is a chemical reaction diagram illustrating three processes of synthesizing thioether-linked flame-retardant butanetriol-derived small molecules, according to some embodiments of the present disclosure.

FIG. 5H is a chemical reaction diagram illustrating three processes 500-18, 500-19, and 500-20 of synthesizing thioether-linked flame-retardant butanetriol-derived small molecule, according to some embodiments of the present disclosure. Each process is a thiol-ene reaction between the allyl-substituted flame-retardant butanetriol-derived small molecule 568 and a flame-retardant thiol molecule. The syntheses and structures of the flame-retardant thiol molecules are discussed in greater detail with regard to FIGS. 3C and 3D.

In process 500-18, the allyl-substituted flame-retardant butanetriol-derived small molecule 568 is reacted with the hydroxy-derived flame-retardant thiol molecule 360 under UV light. The resulting thioether-linked flame-retardant butanetriol-derived small molecule 572 has an $R_3$ group 514 that corresponds to the hydroxy-derived flame-retardant thiol molecule 360. In process 500-19, the allyl-substituted flame-retardant butanetriol-derived small molecule 568 is reacted with the amino-derived flame-retardant thiol molecule 375 in a methanol (MeOH) solution under UV light. The resulting thioether-linked flame-retardant butanetriol-derived small molecule 576 has an $R_4$ group 518 that corresponds to the amino-derived flame-retardant thiol molecule 375. In process 500-20, the allyl-substituted flame-retardant butanetriol-derived small molecule 568 is reacted with the carboxylic acid-derived flame-retardant thiol molecule 345 under UV light in a pH 9 methanol (MeOH) solution. The resulting thioether-linked flame-retardant butanetriol-derived small molecule 580 has an $R_5$ group 522 that corresponds to the carboxylic acid-derived flame-retardant thiol molecule 345.

In some embodiments, the processes of forming the flame-retardant thiol molecules illustrated in FIGS. 3C and 3D and the substituted flame-retardant aconitic acid-derived small molecules illustrated in FIGS. 5A, 5C, and 5E are carried out with a mixture of either both DPCPa 207-1 and DPCPo 207-2 or both phosphate- 205-1 and phosphonate-based 205-2 flame-retardant molecules. Carrying out processes 300-5, -300-7, 500-1, 500-6, 500-11, and 500-16 with a mixture of DPCPa 207-1 and DPCPo 207-2 can result in the production of phenyl-substituted flame-retardant aconitic acid-derived small molecules with both phosphoryl and phosphonyl FR groups. Likewise, combining the phosphate- 205-1 and phosphonate-based 205-2 flame retardant molecules in processes 500-2, 500-7, 500-12, and 500-17 can result in allyl-substituted flame-retardant aconitic acid aconitic acid-derived small molecules with both phosphoryl and phosphonyl FR groups.

However, in some instances, adding a mixture of phosphate- 205-1 and phosphonate-based 205-2 flame retardant molecules (or DPCPa 207-1 and DPCPo 207-2) can result in the production of flame-retardant aconitic acid-derived small molecules with all phosphoryl or all phosphonyl FR groups. Additionally, adding both phosphate- and phosphonate-based molecules to the reaction can yield a mixture of products that includes some combination of flame-retardant aconitic acid-derived small molecules with either all phosphoryl or all phosphonyl FR groups and flame-retardant aconitic acid-derived small molecules with both phosphoryl and phosphonyl FR groups.

Further, in some embodiments, the processes of forming thioether-linked flame-retardant aconitic acid-derived small molecules illustrated in FIGS. 5B, 5D, 5F, and 5H are carried out with mixtures of more than one type of thiol molecule. This can result in the production of thioether-linked flame-retardant aconitic acid-derived small molecules that have two different types of thioether-linked FR group. However, in some instances, adding more than one type of thiol molecule to the reaction mixture can result in thioether-linked flame-retardant aconitic acid-derived small molecules that have two identical thioether-linked FR groups. Adding more than one type of thiol molecule to the reaction mixture can also result in a mixture of products that includes some combination of aconitic acid-derived small molecules with either two different thioether-linked FR groups or two identical thioether-linked FR groups.

The flame-retardant aconitic acid-derived small molecules disclosed herein can be combined with polymers and resins that have a variety of applications. These polymers and resins are made flame-retardant by the addition of the flame-retardant aconitic acid-derived small molecules. The flame-retardant polymers and resins can be used in a number of devices. The flame-retardant aconitic acid-derived small molecules can be added to the polymers and resins during blending, curing, foaming, extrusion, or other processing techniques.

One example of a polymer that can be made flame-retardant by the addition of flame-retardant aconitic acid-derived small molecules is polycarbonate-acrylonitrile butadiene styrene (PC-ABS), a plastic that is often used in electronics hardware. Flame-retardant aconitic acid-derived small molecules can also be incorporated into polyurethane. Polyurethane is a versatile polymer used in applications that include acoustic dampening, cushioning, plastics, synthetic fibers, insulation, adhesives, etc. The aconitic acid-based flame-resistant small molecules can also be added to adhesives such as bio-adhesives, elastomers, thermoplastics, emulsions, thermosets, etc. Further, materials containing the aconitic acid-based flame-resistant small molecules can be incorporated into various devices with electronic components that can include printed circuit boards (PCBs), semiconductors, transistors, optoelectronics, capacitors, resistors, etc.

Resins for printed circuit boards (PCBs) can be made flame-retardant by incorporating aconitic acid-based flame-retardant small molecules. PCBs are electrical circuits that can be found in most types of electronic device, and they support and electronically connect electrical components in the device. PCBs are formed by etching a copper conductive layer laminated onto an insulating substrate. The insulating substrate can be a laminate comprising a resin and a fiber. Many resins in PCBs contain a polymer, such as an epoxy, a polyhydroxyurethane, a polycarbonate, a polyester, a polyacrylate, a polyimide, a polyamide, a polyurea, a poly(vinylester), etc. Flame-retardant aconitic acid-derived small molecules can be added to the resin in order to prevent the PCB from catching fire when exposed to high temperature environments or electrical power overloads.

It should be noted that, in some embodiments, the compounds described herein can contain one or more chiral centers. These can include racemic mixtures, diastereomers, enantiomers, and mixtures containing one or more stereoisomer. Further, the disclosed compounds can encompass racemic forms of the compounds in addition to individual stereoisomers, as well as mixtures containing any of these.

The synthetic processes discussed herein and their accompanying drawings are prophetic examples, and are not limiting; they can vary in reaction conditions, components, methods, etc. In addition, the reaction conditions can optionally be changed over the course of a process. Further, in some embodiments, processes can be added or omitted while still remaining within the scope of the disclosure, as will be understood by a person of ordinary skill in the art.

What is claimed is:

1. A flame-retardant aconitic acid-derived small molecule comprising:
   at least one phosphorus-based moiety with a formula selected from a group of formulas consisting of:

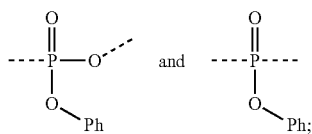

and
at least one substituent bound to the at least one phosphorus-based moiety.

2. The flame-retardant aconitic acid-derived small molecule of claim 1, wherein the flame-retardant aconitic acid-derived small molecule is selected from a group of aconitic acid-derived small molecules with formulas of:

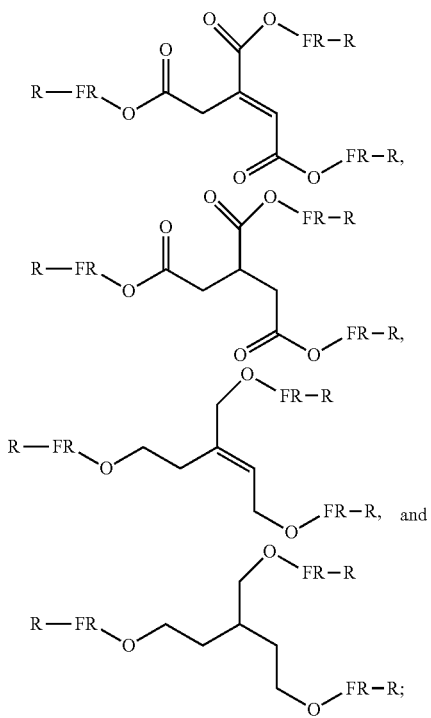

wherein FR is the at least one phosphorus-based moiety; and wherein R is a substituent selected from a group consisting of a phenyl substituent, an allyl substituent, and a thioether substituent.

3. The flame-retardant aconitic acid-derived small molecule of claim 2, wherein the thioether substituent is selected from a group consisting of thioether substituents with formulas of:

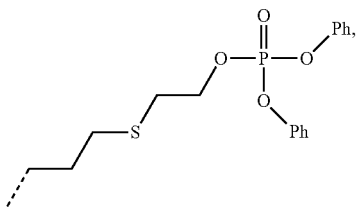

-continued

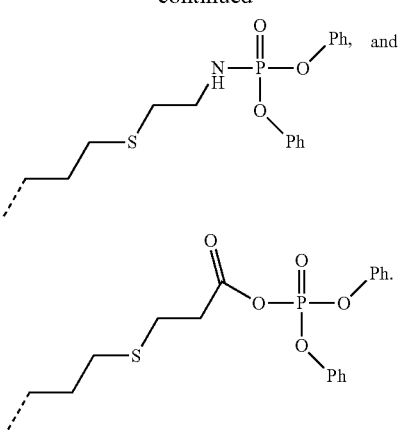

4. The flame-retardant aconitic acid-derived small molecule of claim 1, wherein the flame-retardant aconitic acid-derived small molecule is synthesized from aconitic acid obtained from a bio-based source.

5. The flame-retardant aconitic acid-derived small molecule of claim 1, wherein the flame-retardant aconitic acid-derived small molecule is blended with a polymer.

6. A process of forming a flame-retardant polymer, comprising:
forming a phosphorus-based flame-retardant molecule;
forming an aconitic acid derivative selected from a group consisting of carboxysuccinic acid, 2-(hydroxymethyl)-1,4-butenediol, and 2-(hydroxymethyl)-1,4-butanediol;
chemically reacting the aconitic acid derivative with the phosphorus-based flame-retardant molecule to form an aconitic acid-based flame-retardant small molecule; and
combining the flame-retardant aconitic acid-derived small molecule with a polymer to form the flame-retardant polymer.

7. The process of claim 6, wherein the aconitic acid derivative is synthesized from aconitic acid obtained from a bio-based source.

8. The process of claim 7, wherein the bio-based source is citric acid.

9. The process of claim 6, wherein the phosphorus-based flame-retardant molecule is selected from a group consisting of phosphorus-based molecules with formulas of:

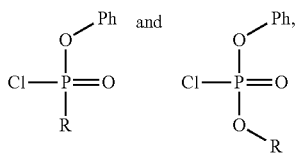

wherein R is a substituent selected from a group consisting of a phenyl substituent and an allyl substituent.

10. The process of claim 6, wherein the phosphorus-based flame-retardant molecule is a thiol molecule with a formula of:

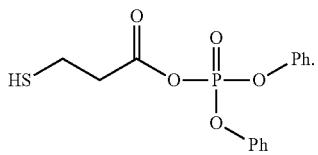 [SMILES: O=C(CCS)OP(=O)(Oc1ccccc1)Oc1ccccc1]

11. The process of claim 6, wherein the phosphorus-based flame-retardant molecule is a thiol molecule with a formula of:

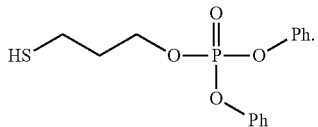 [SMILES: O=P(OCCCS)(Oc1ccccc1)Oc1ccccc1]

12. The process of claim 6, wherein the phosphorus-based flame-retardant molecule is a thiol molecule with a formula of:

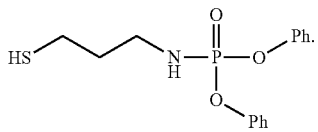 [SMILES: O=P(NCCCS)(Oc1ccccc1)Oc1ccccc1]

13. An article of manufacture, comprising:
a material containing a flame-retardant aconitic acid-derived small molecule, comprising:
at least one phosphorus-based moiety with a formula selected from a group of formulas consisting of:

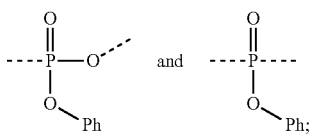

and
at least one substituent bound to the at least one phosphorus-based moiety.

14. The article of manufacture of claim 13, wherein the material is a resin in a printed circuit board.

15. The article of manufacture of claim 13, wherein the flame-retardant aconitic acid derived small molecules is synthesized from aconitic obtained from a bio-based source.

16. The article of manufacture of claim 13, wherein the material is selected from a group consisting of an adhesive and a plastic.

17. The article of manufacture of claim 13, wherein the material is a polymer selected from a group consisting of polyurethane, an epoxy, a polyhydroxyurethane, a polycarbonate, a polyester, a polyacrylate, a polyimide, a polyamide, a polyurea, and a poly(vinyl-ester).

* * * * *